US00PP35627P2

(12) United States Plant Patent
Hansen

(10) Patent No.: US PP35,627 P2
(45) Date of Patent: Jan. 30, 2024

(54) ***X MANGAVE* PLANT NAMED 'WHALE SHARK'**

(50) Latin Name: **x *Mangave***
Varietal Denomination: Whale Shark

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 18/445,123

(22) Filed: Apr. 17, 2023

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 5/12
See application file for complete search history.

*Primary Examiner* — Kent L Bell

(57) ABSTRACT

A new and unique X *Mangave* plant named 'Whale Shark' is characterized by glaucous, variegated, slightly-arching, lanceolate foliage with small semi-flexible marginal teeth on deeply-scalloped margins and apical spines. Leaves have a silver-grey center, creamy-white edge and a minty-green zone between, and develop greyed-purple spotting with strong ultraviolet light. The habit is low, wide, and slightly arching. Plants are useful for landscaping as specimens or en masse or as container plants in the landscape or in the home.

1 Drawing Sheet

Botanical classification: Hybrid *Manfreda* times *Agave* known as x *Mangave*.

Variety denomination: 'Whale Shark'.

STATEMENT REGARDING PRIOR DISCLOSURES UNDER 37 CFR 1.77(B)(6)

No plants of x *Mangave* 'Whale Shark' have been sold, in this country or anywhere in the world, nor has any disclosure of the new plant been made public prior to the filing of this application.

BACKGROUND OF THE INVENTION

The present invention relates to the new and distinct X *Mangave* hybrid plant, X *Mangave* 'Whale Shark' discovered by the inventor at a wholesale perennial nursery in Zeeland. Michigan, USA as an uninduced whole plant mutation of x *Mangave* 'Whale Tale' U.S. Plant Pat. No. 31,060 on Jun. 20, 2019. Through trials at the same nursery, the plant was originally assigned the breeder code 19-51-XMANG-857. The new plant has been successfully asexually propagated by sterile shoot tip tissue culture at the same nursery in Zeeland, Michigan since February 2023. 'Whale Shark' has been found to produce stable and identical plants in successive generations that maintain all the unique characteristics of the original plant.

BRIEF SUMMARY OF THE INVENTION

X *Mangave* 'Whale Shark' differs from its parents as well as all other *Manfreda, Agave*, and X *Mangave* known to the applicant. Compared with the parent, the new plant has leaves that have a broad creamy white margin, a silver-grey center, and an intermediate minty-green longitudinal stripe between.

The most similar cultivars known to the inventor are: x *Mangave* 'Bridal Falls' U.S. Plant Pat. No. 33,080, 'Wavecrest' U.S. Plant Pat. No. 33,489, and 'Life on Mars' U.S. Plant Pat. No. 32,939, 'Navajo Princess' U.S. Plant Pat. No. 31,136, 'Snow Leopard' U.S. Plant Pat. No. 31,137, and 'Niagara Falls' U.S. Plant patent application Ser. No. 18/445,127, co-pending.

'Bridal Falls' has a whiter variegated margin with less-glaucous, darker green in the center, and the leaves arch more and have more prominent marginal teeth. 'Wavecrest' has a smaller habit and shorter foliage with greater indentations at the toothed margin. 'Life on Mars' has a more upright and larger habit with broader, flatter foliage, more reddish spotting covering more of the foliage, the leaves are less glaucous, and the teeth are much smaller. 'Navajo Princess' and 'Snow Leopard' are both variegated with creamy-white margins and the foliage is longer, flatter, and with smaller marginal teeth. 'Niagara Falls' has light chartreuse to light yellowish cream variegated margin, a dark green leaf center, slightly smaller marginal teeth, and more longitudinally-folded foliage.

'Whale Tale' has solid silver-grey foliage without marginal variegation.

The new plant, 'Whale Shark', is unique from all of the above cultivars and all *Agave*, X *Mangave* and *Manfreda* known to the inventor by the following combined traits:

1. Low, wide, slightly arching habit;
2. Glaucous, silver-grey foliage develops a glaucous covering and irregular greyed-purple spotting with strong ultraviolet light;
3. Leaves are variegated with a wide creamy-white edge and a minty-green intermediate zone between the edge and center;
4. Moderate growth rate.

BRIEF DESCRIPTION OF THE DRAWINGS

The drawings of x *Mangave* 'Whale Shark' demonstrate the overall appearance of the new plant including the unique traits of a three-year-old plant grown in a greenhouse in Zeeland, Michigan. The colors are as accurate as reasonably possible with color reproductions. Ambient light spectrum, temperature, source, and direction may cause the appearance of minor variations in color.

DETAILED BOTANICAL DESCRIPTION

Figure 1:
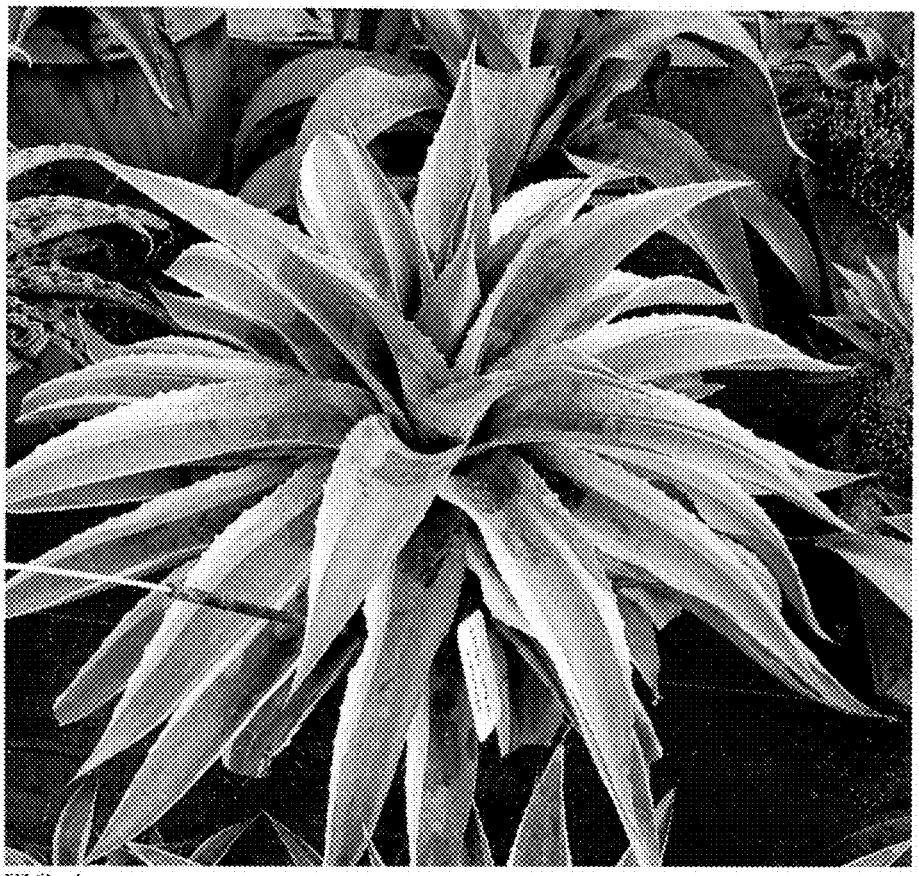
FIG. 1 shows the new plant and foliage from above.
Figure 2:
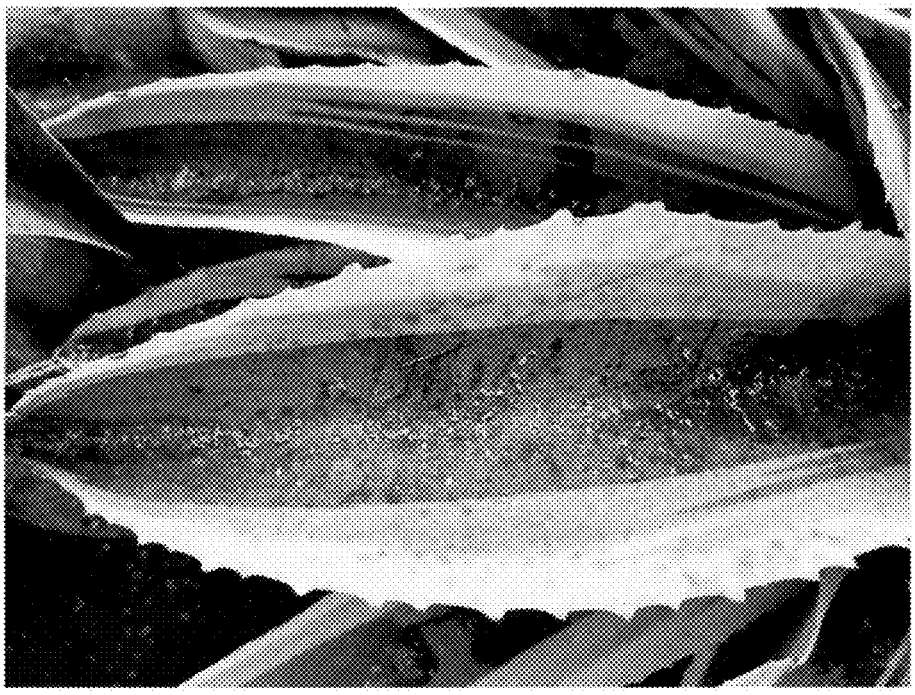
FIG. 2 shows a close-up of the new plant foliage.

The following descriptions and color references are based on the 2015 edition of The Royal Horticultural Society Colour Chart except where common dictionary terms are used. The new plant, X *Mangave* 'Whale Shark', has not been observed under all possible environments. The phenotype may vary slightly with different environmental conditions, such as temperature, light, fertility, moisture, and maturity levels, but without any change in the genotype. The following observations and size descriptions are of a four-year-old plant in a commercial wholesale greenhouse in Zeeland, Michigan with supplemental water and fertilizer as needed.

Parentage: An uninduced whole plant mutation of 'Whale Tale';

Propagation: Division of side shoots and sterile shoot-tip tissue culture;

Time to initiate roots from tissue culture: About 21 days;

Growth rate: Moderate;

Crop time: About 14 to 18 weeks to finish in a 3.8-liter container from a 35 mm tissue culture growing at about 21° C.;

Rooting habit: Fleshy, lightly branching, with roots up to 30 cm long;

Root color: Nearest RHS 158D depending on soil components;

Plant shape and habit: Succulent, herbaceous, freeze-tender perennial with basal rosettes of about 48 leaves radially emerging and outwardly and distally arching from central stem extending below the base of the plant when grown in containers, producing a radially-symmetrical, short, mound;

Plant size: Foliage height about 30 cm tall and about 92 cm wide at the widest point slightly below soil line in container;

Foliage description: Lanceolate; simple; margins scalloped with small firm teeth; apex spinose; base truncate, sessile, clasping; flat to moderately conduplicate; bi-laterally symmetrical;

Leaf size: To about 43 cm long, about 10 cm wide near base, and 9 mm thick, average about 38 cm long, 8.5 cm wide, and 7 mm thick; variegated adaxial margin to about 17 mm wide near middle, center to about 25 mm wide, and intermediate minty-green zone to about 17 mm; variegated abaxial margin to about 12 mm wide near middle, center to about 40 mm wide, and intermediate zone to about 3 mm wide;

Marginal teeth: To about 3 mm long on scalloped indentations about 4 mm deep and about 10 mm apart;

Marginal teeth color: On young leaves between RHS 158A and RHS 158B, maturing to nearest RHS 200C;

Spots: On adaxial and abaxial, generally circular although sometimes overlapping; to about 4 mm across, average about 2 mm across, more strongly pigmented with intense ultraviolet light;

Foliage fragrance: None observed;

Leaf blade color:

*Adaxial* (*young*).—Center blend between nearest RHS N138C and RHS 189B with spots variable nearest RHS NN137D or not yet developed; margin between RHS 147C and RHS 191B with spots not yet developed; intermediate zone not developed enough to be distinguished.

*Abaxial* (*young*).—Center blend between nearest RHS N138C and RHS 189B with spots variable nearest RHS NN137D or not yet developed; margin between RHS 147C and RHS 191B with spots not yet developed; intermediate zone not developed enough to be distinguished.

*Adaxial* (*mature*).—Center blend between nearest RHS 189A and RHS 189B with developing spots variable between RHS N187C and RHS N187A with intense ultraviolet light; margin between RHS 158B and RHS 19C with developing spots between RHS 59D and a blend of RHS 59D and RHS 158B; intermediate zone between RHS 190A and RHS 194B with developing spots between 59D and a blend between RHS 190A and RHS 59D.

*Abaxial* (*mature*).—Center blend between nearest RHS N138C and RHS 190B with developing spots variable between RHS NN137D and RHS N187B with more ultraviolet light exposure; margin between RHS 158B and RHS 19C with developing spots between RHS 59D and a blend of RHS 59D and RHS 158B; intermediate zone between RHS 190A and RHS 194B with developing spots between 59D and a blend between RHS 190A and RHS 59D.

Apical spine or mucro: Sharp and slightly flexible; average about 9 mm long and about 1 mm wide at base;

Apical spine or mucro color: Between RHS 166B and RHS 169A on young expanding leaves, and maturing to nearest RHS 200B;

Petiole: Sessile;

Veins: Parallel; not distinct abaxial or adaxial;

Stem: Terete; covered with leaves; to about 5.5 cm across and extending to about 4 cm above soil; without branching; attitude upwards, erect;

Flowers have not yet been observed.

Fruit and seed have not yet been observed.

Disease resistance: X *Mangave* 'Whale Shark' has not been observed to be resistant to diseases beyond that which is normal for X *Mangave, Agave* or *Manfreda*. The plant is xeromorphic and survives well with minimal water once established. The new plant is hardy at least from USDA zone 8 to 11. Full extent of winter hardiness has not been tested.

It is claimed:

1. A new and distinct cultivar of ornamental X *Mangave* plant named 'Whale Shark' as herein described and illustrated, suitable for the garden or as a potted plant in the garden or home.

* * * * *